United States Patent [19]

Man

[11] Patent Number: Plant 7,025

[45] Date of Patent: Sep. 12, 1989

[54] DISTINCT VARIETY OF BEGONIA PLANT NAMED PINK BEAUTY

[75] Inventor: Jan Man, Lisse, Netherlands

[73] Assignee: Oglevee Ltd., Connellsville, Pa.

[21] Appl. No.: 251,685

[22] Filed: Sep. 29, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

The new cultivar is generally characterized by its superior compact growth and flowering ability. The pink bloom and the rose-bud type immature bloom compliment the foliage. The bloom is long lasting and continue to produce buds.

1 Drawing Sheet

BACKGROUND OF THE NEW PLANT

The present invention comprises a new and distinct cultivar of *Begonia*×*hiemalis* known by the varietal name of Pink Beauty. The new cultivar is a sport of the cultivar Ilonka (U.S. Plant Pat. No. 6,203). The new cultivar has the general appearance of Ilonka. However, the new cultivar is slightly taller and has a more compact form than Ilonka. The tonality of the light pink bloom differs from the peach bloom of Ilonka.

The new cultivar was discovered in August of 1984 at Limaplant b.v. in Lisse, Holland; was first asexually reproduced by cuttings at Limaplant b.v. in Lisse, Holland; and has been repeatedly asexually reproduced by cutting for Oglevee Ltd. in Connellsville, Pa. It has been found to retain its distinctive characteristics through successive propagations.

The new cultivar is generally characterized by its superior compact growth and flowering ability. The pink bloom and the rose-bud type immature bloom compliment the foliage. The bloom is long lasting and continues to produce buds.

The new cultivar, when grown in a greenhouse in Connellsville, Pa., has a response time of 9 to 10 weeks from a well-rooted cutting to a flowering finished plant in a six inch pot (no pinch).

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Ltd. in Connellsville, Pa. The plant history was taken on ten week plants blossomed under natural light in a greenhouse and grown under temperature conditions of 68° F. night and day. The plants were potted Feb. 2, 1988 in a peat-lite mix and fertilized with a mixture of 20N-10-20K. Color readings were taken indoors under 200 footcandles of cool white fluorescent tubes. Color references are to the R.H.S. Colour Chart of The Royal Horticultural Society of London, unless noted differently.

Botanical Classification: *Begonia*×*hiemalis.*

Flower:

*Fully expanded.*—5.5 cm. in diameter; side view: flattened oval in appearance.

*Borne.*—Compound dichasium (cyme).

*Stems.*—Strong, medium compact stems, average stem width 0.5 to 1.5 cm. in diameter; color yellow-green group 144C.

*Form.*—Semi-double to fully double. Each flower generally has 2 sepals, 5 petals, 3 to 6 petaloids (each group may vary ±1 structure).

*Permanence.*—Very long lasting bloom, average life span of 2 to 3 weeks.

Color:

*Tonality from a distance.*—Pink.

*Front of petals.*—Outer margin red group 47D and blends to center of petal which is red group 41C.

*Reverse of petals.*—Red group 50D which lightens slightly toward the base.

*Base of petals.*—The inward most part of the base is characterized by yellow-green group 145D.

*Throat.*—None observed.

*Discoloration.*—None.

*Other Comments.*—Older flower buds on outside margin characterized by red group 50C and lightens to the base which is characterized by yellow-green group 145C at very base of bud.

Petals:

*Texture.*—Crepe paper like (gentle crinkles).

*Appearance.*—Oval.

*Arrangement.*—Semi to fully double.

*Persistence.*—Very good, flowers last a long time and plant will continue to produce new buds.

*Fragrance.*—None observed.

Reproductive organs: All reproductive organs have formed into petaloids. Anthers, filament, pollen, style and ovaries could not be observed.

Plant:

*Form.*—Short, very compact, internodes 2.0 to 2.5 cm. apart; good basal branching. Strong stems give good support.

*Growth.*—Very vigorous.

*Height from soil line.*—18 to 20 cm. in 10 weeks (no pinch, no cycocel).

*Spread.*—20 to 22 cm. in 10 weeks (no pinch, no cycocel).

Foliage:

*Size.*—Average length of 12 cm. and average width of 10 cm. on leaves 3 nodes up from base of stem.

*Quantity.*—Very abundant.

*Shape.*—Acute tip with irregularly lobed attachment; edge is slightly doubly serrate.

*Top side.*—Green group 137A.

*Underside.*—Green group 138B.

*Ribs and veins.*—Smooth on top side, raised on lower side, lower side veins only area on leaf where visible tricomes (hairs) appear.

*Rib and vein color.*—Top side: yellow-green group 144B; bottom: yellow-green group 146D.

*Margin.*—None.

*Stipules.*—None.

*Texture.*—Top: smooth, shiny and leathery; bottom: matt finish with raised veins.

I claim:

1. A new and distinct variety of begonia characterized by superior compact growth, flowering ability, long lasting bloom and continuous budding and pink bloom with rose-bud type immature bloom compliments the foliage as described and shown herein.

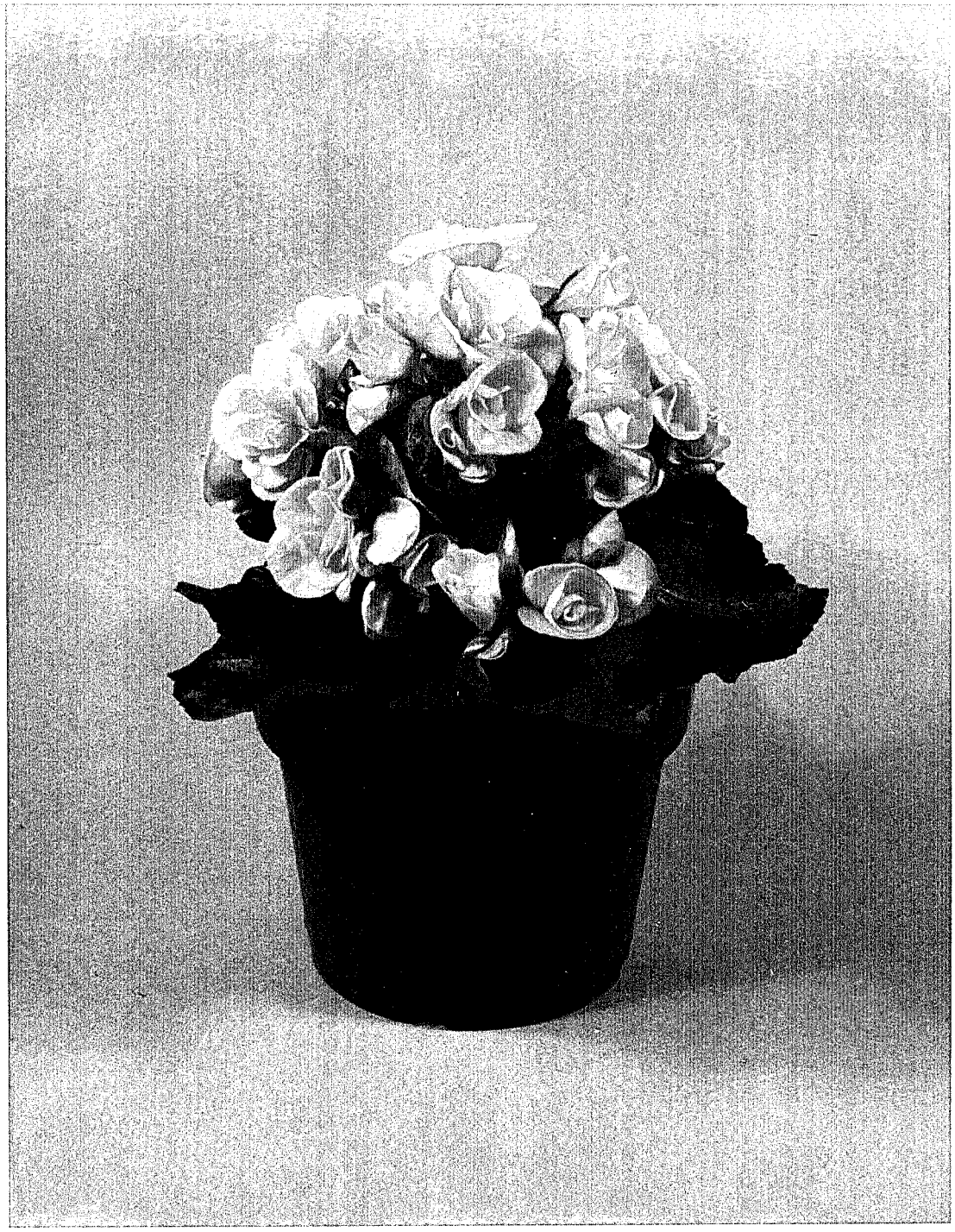

* * * * *